United States Patent [19]
Nelson et al.

[11] Patent Number: 5,016,196
[45] Date of Patent: May 14, 1991

[54] RAIN SAMPLING DEVICE

[75] Inventors: Danny A. Nelson; Stanley D. Tomich, both of Richland; Donald W. Glover, Prosser; Errol V. Allen, Benton City; Jeremy M. Hales, Kennewick; Marshall T. Dana, Richland, all of Wash.

[73] Assignee: Battelle Memorial Institute, Richland, Wash.

[21] Appl. No.: 476,124

[22] Filed: Feb. 2, 1990

Related U.S. Application Data

[63] Continuation of Ser. No. 198,192, May 24, 1988, abandoned.

[51] Int. Cl.[5] .................... G06F 15/20; G06F 15/54; G01W 1/14; G08B 21/00
[52] U.S. Cl. ................................ 364/550; 73/171; 340/602; 364/420
[58] Field of Search ............ 346/33 R; 364/420, 550, 364/478; 73/170 R, 171, 189; 340/601, 602

[56] References Cited

U.S. PATENT DOCUMENTS

| | | | |
|---|---|---|---|
| 4,140,011 | 2/1979 | Krupa et al. | 73/171 |
| 4,245,499 | 1/1981 | Nguyen et al. | 346/33 R |
| 4,613,938 | 9/1986 | Hansen et al. | 364/420 |
| 4,665,743 | 5/1987 | Masniere et al. | 73/170 R |
| 4,697,462 | 10/1987 | Daube, Jr. et al. | 73/170 R |
| 4,698,748 | 10/1987 | Juzswik et al. | 364/707 |
| 4,732,037 | 3/1988 | Daube, Jr. et al. | 73/171 |
| 4,747,041 | 5/1988 | Engel et al. | 364/707 |
| 4,780,843 | 10/1988 | Tietjen | 364/707 |

OTHER PUBLICATIONS

Journal Applied Meteorology, Oct. 1979 (V18 N10); "Digital Recording System for Tipping Bucket Raingages"; J. L. Thomas et al; pp. 1376-1379.
Water, Air & Soil Pollution, Feb. 1978; "Automatic Sequential Rain Sampler"; C. Ronneau et al.; pp. 171-176.
Atmospheric Envir. 1979 (V13 N1); "Automatic Sequential Precipitation Sampler"; G. S. Raynor et al.; pp. 149-155.
Water, Air & Soil Pollution Jun. 1980 (V13N2); "Draft, Construction & Operation of a Sequental Rain Sampler"; W. A. H. Asman; pp. 235-245.
"An Automatic Sequential Rainfall Sampler", Gray et al., *Review of Scientific Instruments*, vol. 45, No. 12, Dec. 1974, pp. 1517-1519.
*Patent Abstracts of Japan*, vol. vol. 6, No. 13(P-99)(891), Jan. 26, 1982, "Rain Gauge of Automatic Water Storage", Patent 56-137181(A), Oct. 26, 1981, Application No. 55-40670, Toshio Takagi.

*Primary Examiner*—Kevin J. Teska
*Attorney, Agent, or Firm*—Dellett, Smith-Hill and Bedell

[57] ABSTRACT

The present invention constitutes a rain sampling device adapted for independent operation at locations remote from the user which allows rainfall to be sampled in accordance with any schedule desired by the user. The rain sampling device includes a mechanism for directing wet precipitation into a chamber, a chamber for temporarily holding the precipitation during the process of collection, a valve mechanism for controllably releasing samples of said precipitation from said chamber, a means for distributing the samples released from the holding chamber into vessels adapted for permanently retaining these samples, and an electrical mechanism for regulating the operation of the device.

10 Claims, 6 Drawing Sheets

RAIN SAMPLING DEVICE

This invention was made with government support under contract number DE-AC06-76RLO 1830, awarded by the U.S. Department of Energy. The government has certain rights in the invention.

This is a continuation of application Ser. No. 07/198,192, filed May 24, 1988, and now abandoned.

BACKGROUND OF THE INVENTION

The present invention relates to weather monitoring equipment and more particularly to rain sampling devices capable of independent operation at remote locations.

In recent years concerns have arisen about the chemical composition of rainfall. In particular, acid rain has been shown to have a detrimental impact on the environment. Consequently, it has become important to be able to sample rainfall according to predetermined schedules at remote locations. Rain sampling devices have been built in the past, but they have tended to be comparatively complex and expensive devices which have been difficult to maintain in the field. Further, past rain sampling devices have allowed for relatively short periods of operation, since by design they have required significant amounts of battery power to be supplied on a continuous basis.

It is therefore an object of the present invention to provide a rain sampling device which is of comparatively simple construction and therefore has a greater degree of functional reliability.

It is another object of the present invention to provide a rain sampling device which conserves electrical power during periods when the device need not be fully operative.

It is a further object of the present invention to provide a rain sampling device which is inexpensive to construct yet efficiently accomplishes its purposes.

SUMMARY OF THE INVENTION

The present invention constitutes a rain sampling device adapted for independent operation at locations remote from the user which allows rainfall to be sampled in accordance with any predetermined schedule desired by the user. The rain sampling device includes a mechanism for directing wet precipitation into a chamber, a chamber for temporarily holding the precipitation during the process of collection, a valve mechanism for releasing samples of said precipitation from said chamber in response to a control signal, an electrical mechanism for controlling the operation of the device and a means for distributing the samples released from the holding chamber into vessels adapted for permanently retaining the samples.

In the preferred embodiment, the valve mechanism includes a magnetically actuated plunger which alternatively seals the exit or entrance to the holding chamber in accordance with power being applied to a coil. The electrical control means includes a programmable microcomputer which is adapted for allowing the user to implement any sampling schedule desired. The sampling device also includes a mechanism for activating and deactivating the majority of the components in the system by engaging and disengaging power to these components. The power is disengaged in order to conserve energy whenever samples are not required to be taken and is engaged only when precipitation is sensed by a moisture detector and/or start-up signals are provided by a real-time clock device. The preferred embodiment of the rain sampling device further includes a ring gear rotatable in accordance with signals from said electrical control means having a special channel for distributing precipitation samples into different ones of the retaining vessels.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT

Figure 1:
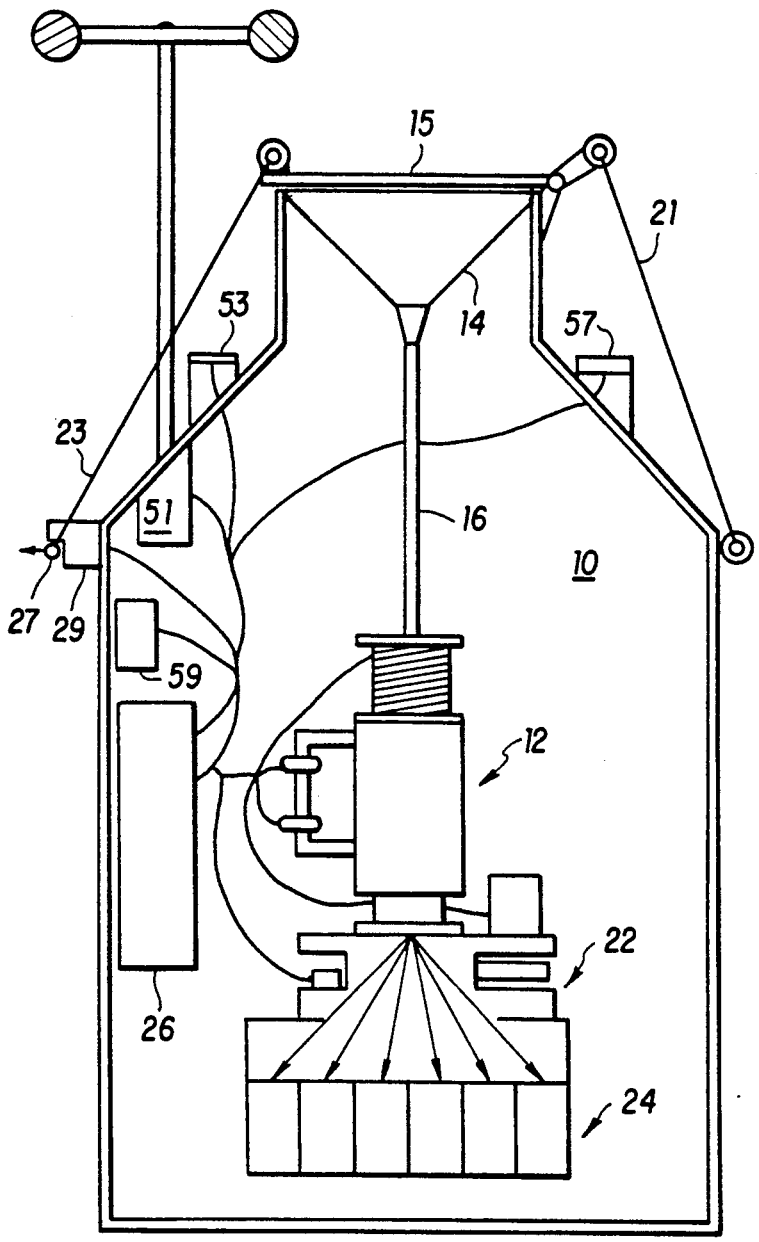
FIG. 1 is a diagrammatic side view of the rain sampling device of the present invention.

Referring now to FIG. 1, the rain sampling device 10 of the present invention includes a chamber 12 in which wet precipitation (rain) may be collected. The chamber 12 receives precipitation by way of a funnel 14 and tube 16 which divert precipitation from a broad area into the chamber 12. A hinged lid 15 is attached to the device 10 near the top of the funnel 14 for preventing precipitation from entering the funnel 14 and being collected during periods when samples are not desired to be taken. A valve mechanism 20 (not shown in FIG. 1) is associated with the chamber 12 for releasing samples from the chamber 12 when a sufficient quantity of precipitation has been collected. A dispensing system 22 is secured to the bottom end of the chamber 12 for directing samples released from the chamber 12 into one of several sample retaining vessels 24. A microcomputer system 26 controls the functioning of the device 10 by regulating the operation of the dispensing system 22, the lid 15, and the valve mechanism 20 as will be described hereinafter.

The lid 15 is attached to an elastic cord 21 which supplies tension urging the lid 15 to open. The opposite side of the lid 15 is attached to another cord 23 which is attached to a bar 27 subject to being released from a latching device 29 by the action of a solenoid. When the solenoid is activated, the bar 27 is released and the lid opens allowing precipitation to enter the funnel 14.

Figure 2:
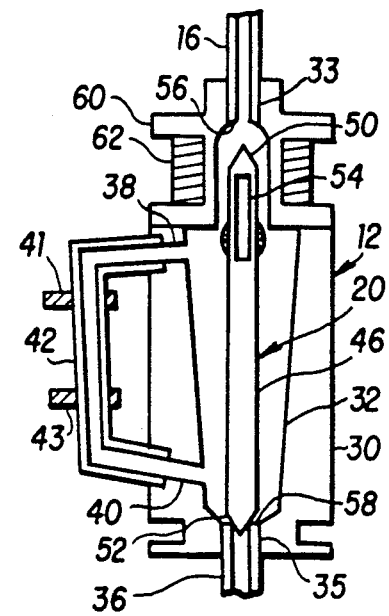
FIG. 2 is a cross-sectional view of the holding chamber and valve mechanism components of the rain sampling device of the present invention.

Referring now to FIG. 2, the chamber 12 comprises a cylindrical body 30 of high density polyethylene having a tapered cavity 32 centered therein. An entrance port 33 and exit port 35 connect the top and bottom ends of the cavity to the tubes 16 and 36, respectively. Also, an upper port 38 and a lower port 40 connect the upper and lower ends of the cavity 32 to a polyethylene viewing tube 42 which extends vertically alongside the chamber 12 and allows convenient detection of the level of the precipitation in the chamber 12. An upper optical sensor 41 and a lower optical sensor 43 detect the actual level of precipitation in the tube 42 and correspondingly in the chamber 12 and provide this information to the microcomputer system 26.

The valve mechanism 20 comprises an elongate plunger 46 also of high-density polyethylene which is conically tapered at both of its ends 50 and 52 and includes a magnetic core 54 toward its upper end 50. The plunger 46 is sized to extend from near the upper end to the lower end of the cavity 32. The ends 50 and 52 of the plunger 46 are tapered at approximately a 26 degree angle so as to efficiently engage the ends 56 and 58 of the tubes 16 and 36 leading from the entrance port 33 and the exit port 35 of the chamber 12, respectively, in order to alternatively seal the cavity 32 at either its top or its bottom end. The tubes 16 and 36 are constructed from medical grade silicon tubing which is pliable enough to efficiently mate with the tapered ends 50 and 52 of the plunger 46 and form water tight joints. The valve mechanism 20 further includes the spool 60 around which an electrical coil 62 of copper wire is wound. The coil 62 operates to attract the magnetic core 54 of the plunger and operate the valve mechanism 20 when power is applied to it.

Figure 4A:
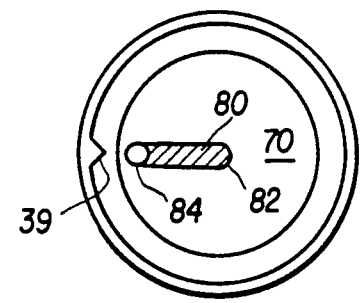
FIGS. 4A and 4B are top and side views of the ring gear element of the rain sampling device of the present invention.
Figure 4B:
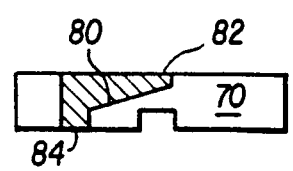
Figure 5:
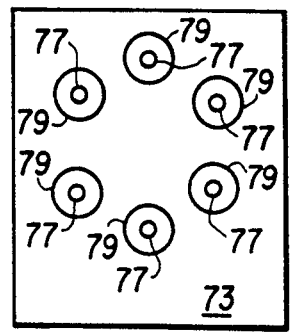
FIG. 5 is a top view of the lower support plate element of the rain sampling device of the present invention.
Figure 3:
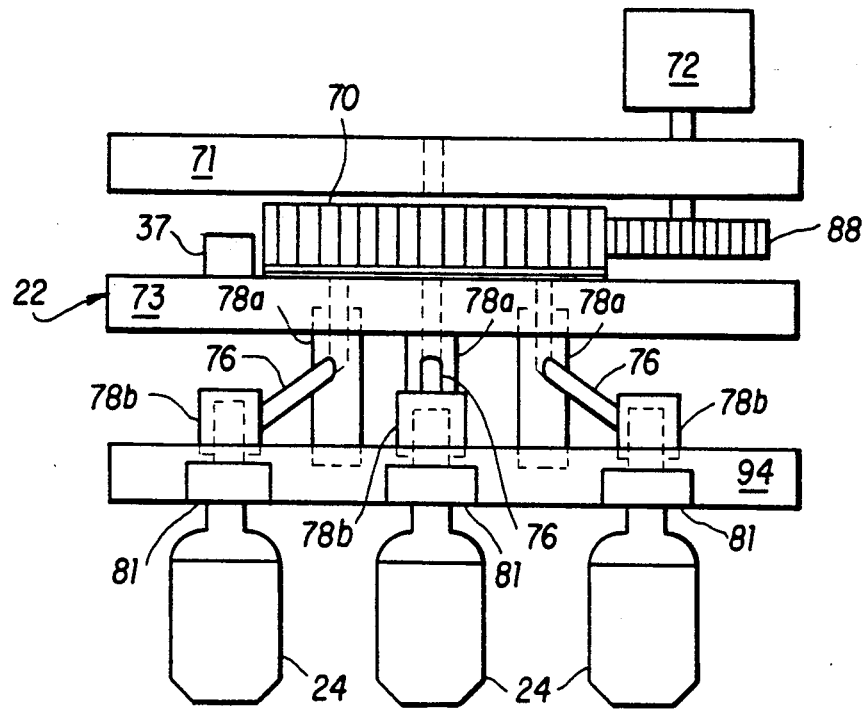
FIG. 3 is a detailed side view of the dispensing system component of the rain sampling device of the present invention.

Referring now to FIG. 3, the dispensing system 22 includes a ring gear 70 which is mounted between upper and lower support plates 71 and 73 and which is driven by a stepper motor 72. As shown in further detail in FIGS. 4a and 4b, the ring gear 70 includes an inclined channel 80 for directing liquid materials to flow away from the center 82 of the gear 70 toward an opening 84 at its periphery under the influence of gravity. The ring gear 70 is engaged by a drive gear 88 mounted on the axle of the stepper motor 72. When the stepper motor 72 is operative, the ring gear 70 is rotated, thereby changing the position to which liquid materials can be directed by the channel 80 and opening 84. As shown in FIG. 5, the lower support plate 73 includes six openings 77 spaced so as to coincide with six different equidistant positions for the opening 84 and through which liquid materials may flow down through the plate 73. A set of O-rings 79 may be mounted concentric to the openings 77 in order to insure a water-tight seal between the gear 70 and plate 73. The optical detector 37 senses the position of the notch 39 shown in FIG. 4A when the notch 39 is adjacent to the detector 37. The ring gear 70 can thereby be aligned and realigned with the openings 77 so that the opening 84 can be accurately positioned over the openings 77 during operation of the device 10.

Referring again to FIG. 3, six vessels 24 (only three of which are actually visible in FIG. 3) for retaining precipitation samples are secured in a circular pattern to a base plate 94 which is located below the lower support plate 73. In the present case, the vessels 24 comprise small-sized bottles constructed from an inert plastic, although other types of vessels such as test tubes could be employed. The vessels 24 are readily mounted using special replaceable inserts 81 so that different types of retaining vessels 24 can be readily mounted to the device 10 simply by changing the inserts 81. Liquid materials are enabled to pass down into the vessels 24 through openings in the inserts 81 in the base plate 94. Each one of the retaining vessels 24 is associated with one of the inclined distribution tubes 76, one of the entrance fittings 78a and one of the exit fittings 78b. The fittings 78a and 78b are mounted in shallow recesses in the upper surface of the base plate 94. Each one of the entrance fittings 78a is adapted to receive liquid materials delivered by way of the opening 84 and one of the openings 77 when the opening 84 is aligned with each such fitting. The fittings 78a direct the liquid materials into the distribution tubes 76. The liquid materials then flow down the tubes 76 to the exit fittings 78b. The exit fittings 78b direct the liquid materials down through one of the openings in the base plate 94 into one of the retaining vessels 24.

Figure 6:
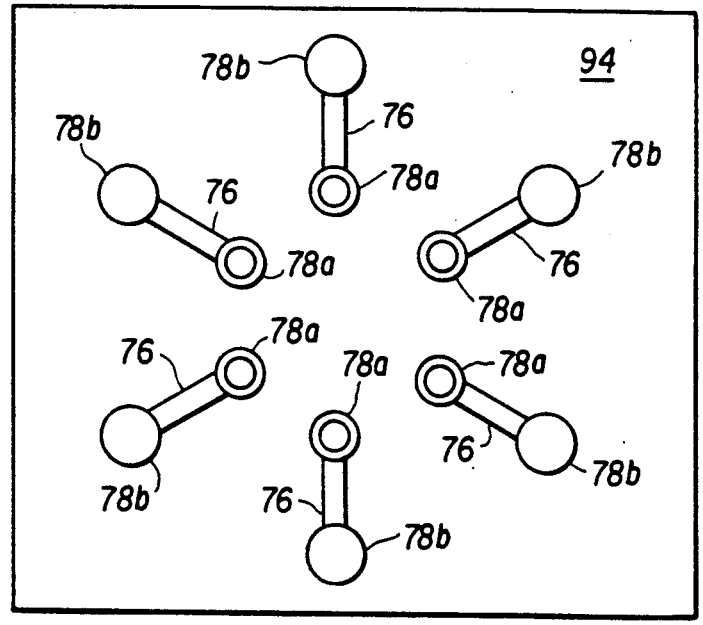
FIG. 6 is a top view of the base plate element and the distribution tubes, entrance fittings and exit fittings associated therewith in the rain sampling device of the present invention.

As shown in FIG. 6, the distribution tubes 76 associated with the retaining vessels 24 extend radially outward around the base plate 94. The distribution tubes 76 and their associated fittings 78a and 78b form passages which allow liquid materials (i.e., wet precipitation) to be separately delivered to each of the vessels 24 from more centrally located positions adjacent to the periphery of the ring gear 70. The precipitation may be targeted for delivery to a specific retaining vessel through the action of the channel 80 when the ring gear 70 is appropriately rotated so that the opening 84 is aligned over the entrance fitting 78a corresponding to the desired retaining vessel.

Figure 7:
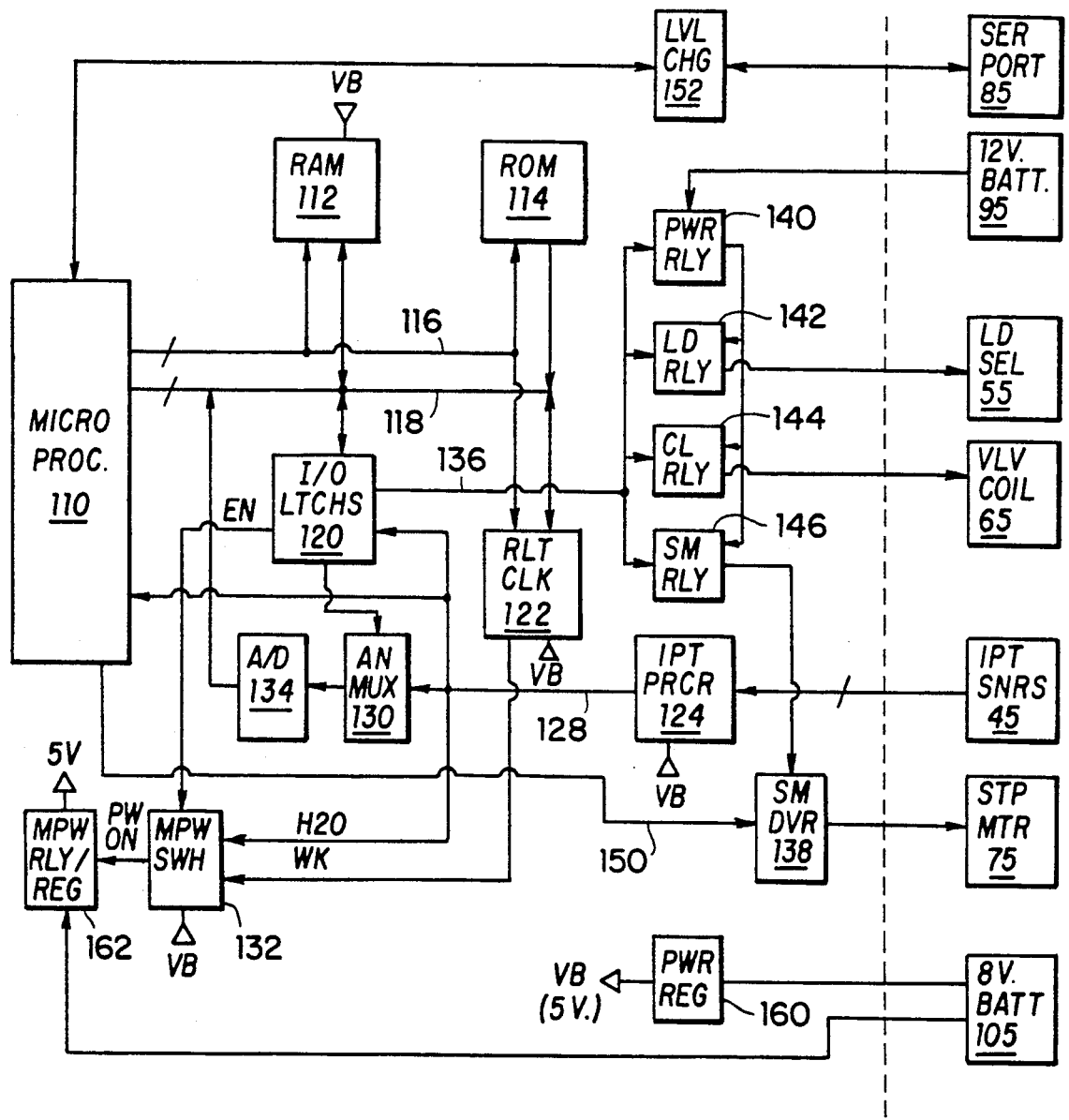
FIG. 7 is an electrical block diagram of the microcomputer system component of the rain sampling device of the present invention.

Referring now to FIG. 7, the microcomputer system 26 includes a microprocessor 110 which is of a conventional type such as an Intel 8052 AH microprocessor. The system 26 also includes a RAM memory component 112 for storing data and a ROM memory component 114 for storing code. Address information is transferred from the microprocessor 110 over the address bus 116. Data is transferred to and from the microprocessor 110 over the data bus 118. A set of I/0 latches 120 handles the input and output of signal data to and from the microprocessor 110.

A real time clock device 122 keeps track of time and has the capability for generating a special signal WK at predetermined times in the future in accordance with scheduling data supplied from the microprocessor 110.

An input signal processing module 124 processes the various signals supplied by the sensory instruments 45 associated with the device 10. The processed input signals are then supplied over the line 128 to either the microprocessor 110, analog multiplexer 130, I/0 latches 120, and/or the main power switch 132.

The input processing module 124 handles signals corresponding to windspeed, the presence of moisture, the amount of solar flux, the temperature, the index position of the ring gear 70 and the level of water in the chamber 12. The windspeed signal is converted from A/C form as supplied by the A/C generator 51 into a square wave which can be supplied directly to the microprocessor 110 for measurement of its pulse frequency which correlates with wind speed. The moisture signal is processed in order to detect any changes in impedance exhibited by a rain detection grid 53, which are indicative of the presence of moisture. The solar flux signal from a photometer 57 is amplified and supplied to the analog-to-digital converter 134 by way of the multiplexer 130. Likewise, the temperature signal from a temperature sensitive resistor 59, and the index signal from the optical detector 37 associated with the ring gear 70, are supplied to the analog-to-digital converter 134 through the multiplexer 130. The signals supplied to the analog-to-digital converter 134 are transformed from analog form to digital format and the information from the signals is then transferred to the microprocessor 110 over the bus 118. The water level signals from the optical sensors 41 and 43 associated with the chamber 12 are compared to predetermined threshold signals in order to generate digital signals indicative of when the water level in the chamber 12 has reached the height of one or the other of these sensors which can be supplied to the microprocessor 110 by way of the latches 120. It should be noted that data from the optical sensors 41 and 43 and temporal information from the clock device 122 are used to form records of the rainfall activity and the timing of the samples taken which are entered into the RAM memory 112 for later use.

In accordance with data provided by the microprocessor 110 the I/0 latches 120 furnish control signals over the line 136 to the relays 140, 142, 144 and 146. The relay 140 controls the supply of 12V power from the battery 95 to other relays 142, 144 and 146. The relays 142, 144 and 146 regulate the supply of power to the solenoid of the lid latching device 27, the valve coil 62 and the stepper motor 72. It should be noted that the operation of the stepper motor 72 is regulated by a stepper motor driver chip 138 in accordance with pulse signals supplied by the microprocessor 110 over the line 150.

The microprocessor 110 is connected to a serial port 85 by way of a level changing (8V–5V and 5V–8V) device 152. The serial port allows the microprocessor 110 to be readily reprogrammed in order to implement different sampling schedules and allows the weather data and information about rainfall activity and the samples taken as recorded by the device 10 to be accessed and read out from the RAM memory component 112.

Power is supplied to the electronic components of the microcomputer system 26 by the 8V battery 105. However, this power is alternatively distributed to the individual components of the system 26 by either the backup power regulator 160 or the main power relay and regulator 162. The backup power regulator 160 supplies power on a continuous basis to the RAM memory component 112, the real time clock device 122, and the elements of the input processing module 124 which process the moisture detection signal. The main power relay and regulator 162 supplies power to all the other electronic components of the system including the microprocessor 110 but does so on an intermittent basis only during periods when these components are required to be operative. The main power relay and regulator 162 is itself controlled by a signal PWON from the main power switch 132. The main power switch 132 receives the signals H20, WK and EN from the input processing module 124, the real-time clock device 122 and the I/0 latches 120, respectively.

The H20 signal indicates that moisture is present and that wet precipitation is occurring. The signal WK indicates that the time has arrived for a prescheduled "wake up" of the device 10. The signal EN is generated by the microprocessor 110 to indicate that operations by the device 10 may temporarily cease and the device may therefore "go to sleep". Accordingly, the signal PWON controls the main power relay and regulator 162 to supply power to the system when either of the signals H20 or WK is asserted. Conversely, the signal PWON controls the power relay and regulator 162 to shut off the power whenever the signal EN is asserted and the signals H20 and WK are not asserted. A majority of the components of the microcomputer system 26 may thereby be shut down during periods of inactivity and substantial amounts of battery power thereby conserved.

In operation, the device 10 is activated when either moisture is detected or when the real-time clock device 122 signals a prescheduled wake up event. Thereafter, the microcomputer system 26 automatically begins execution of a rain sampling program resident in the ROM memory 114. This program directs the components of the device 10 to take readings and record certain weather data and to take rain samples according to whatever schedule has been entered into memory by the operator.

Whenever rain samples are to be taken, the microcomputer system 26 first operates the stepper motor 72 to position the ring gear 70 with reference to the locations of the optical detector 37 and notch 39. The lid 15 is then opened by activating the solenoid associated with the latching device 29. Wet precipitation is allowed to accumulate in the chamber 12 until a sufficient sample is collected as indicated by signals from the optical sensors 41 or 43. The coil 62 is then activated thereby elevating the plunger 46 and releasing the rain sample into the tube 36 which extends through the upper support plate 71 to a point above the center of the ring gear 70. The rain sample flows down the tube 36 into the slot 80 in the ring gear 70 and down through the opening 84. The sample is directed by the position of the ring gear 70 to pass through one of the openings 77 in the lower support plate into one of the entrance fittings 78a. The rain sample then flows through one of the distribution tubes 76 and one of the exit fittings 78b into one of the retaining vessels 24. The coil 62 is deactivated, thereby sealing the exit port 35 and opening the entrance port 33 to the chamber 12. The stepper motor 72 may then be engaged to rotate the ring gear 70 and arrange a pathway to a different one of the retaining vessels 24 whenever a satisfactory amount of wet precipitation has been deposited in one of the retaining vessels.

Figure 8A:
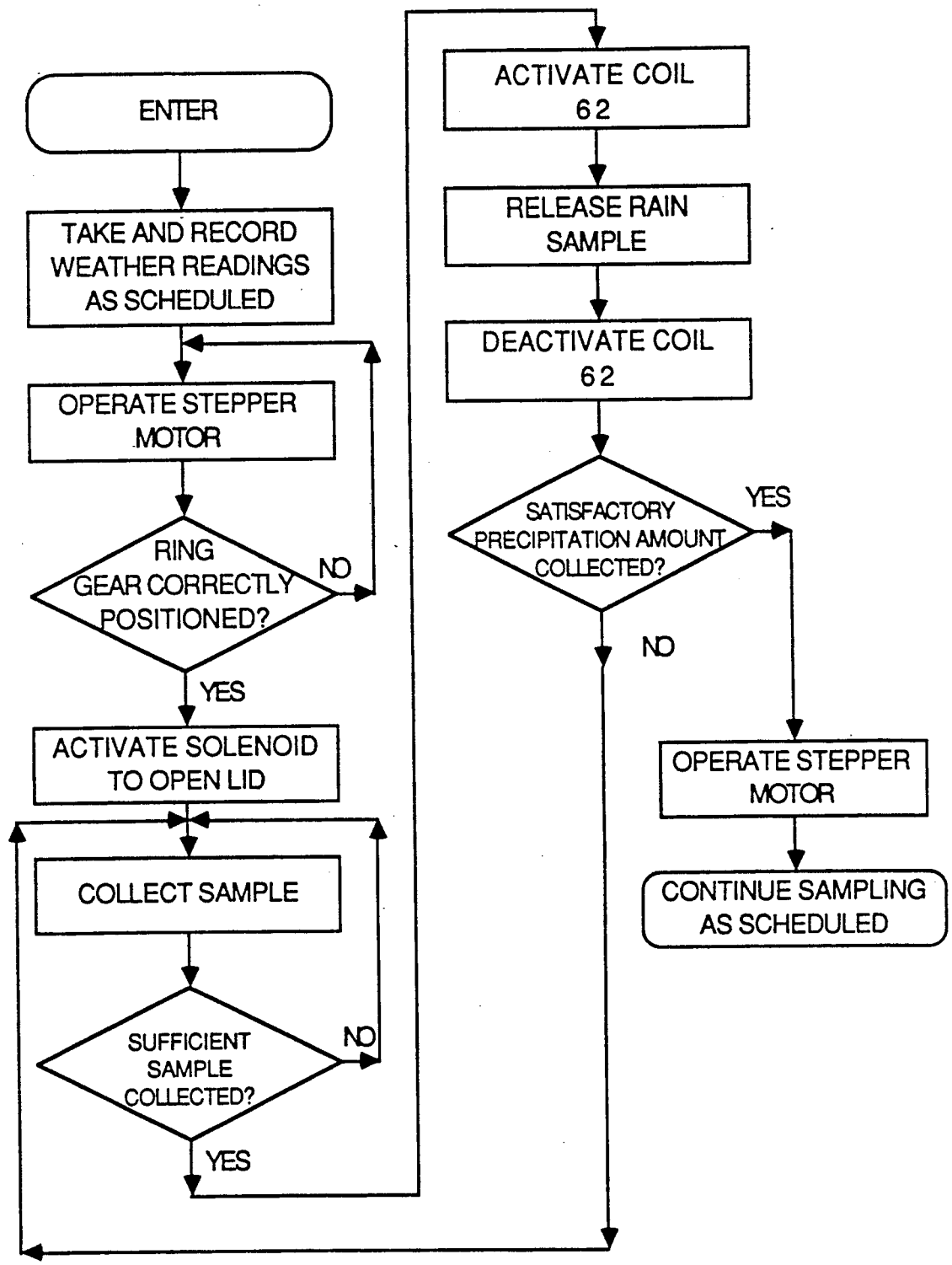
FIG. 8A is a flow diagram illustrating the various operations performed in the rain sampling mode by the microprocessor system component of the rain sampling device of the present invention.
Figure 8B:
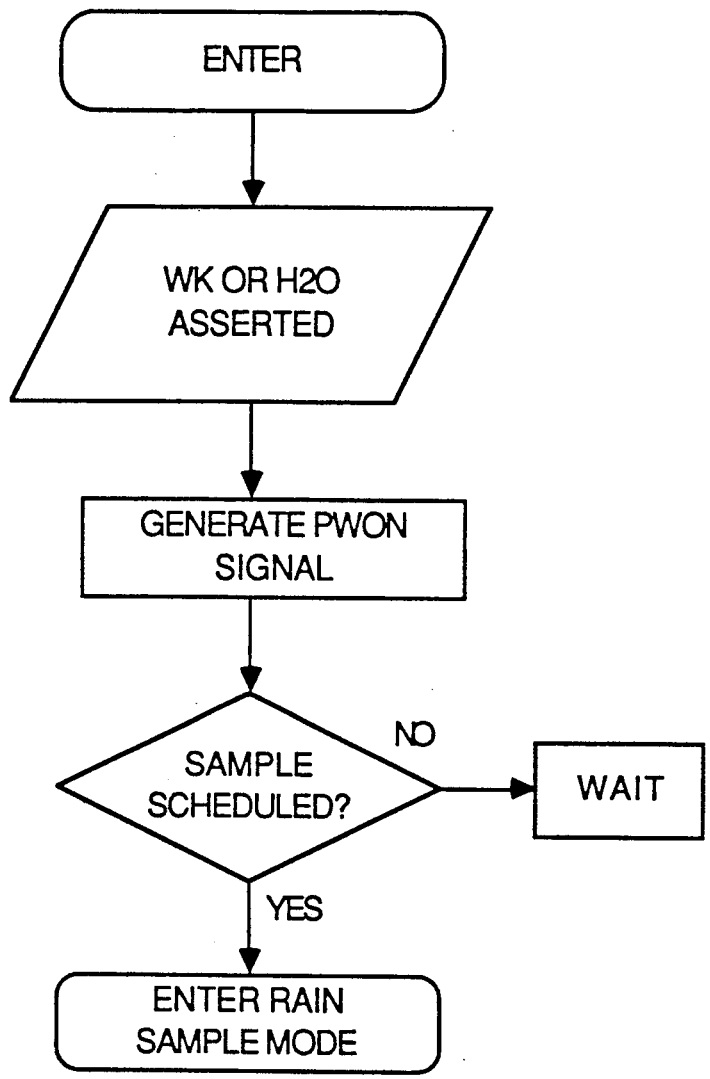
FIG. 8B is a flow diagram of the power up process of the rain sampling device of the present invention.
Figure 8C:
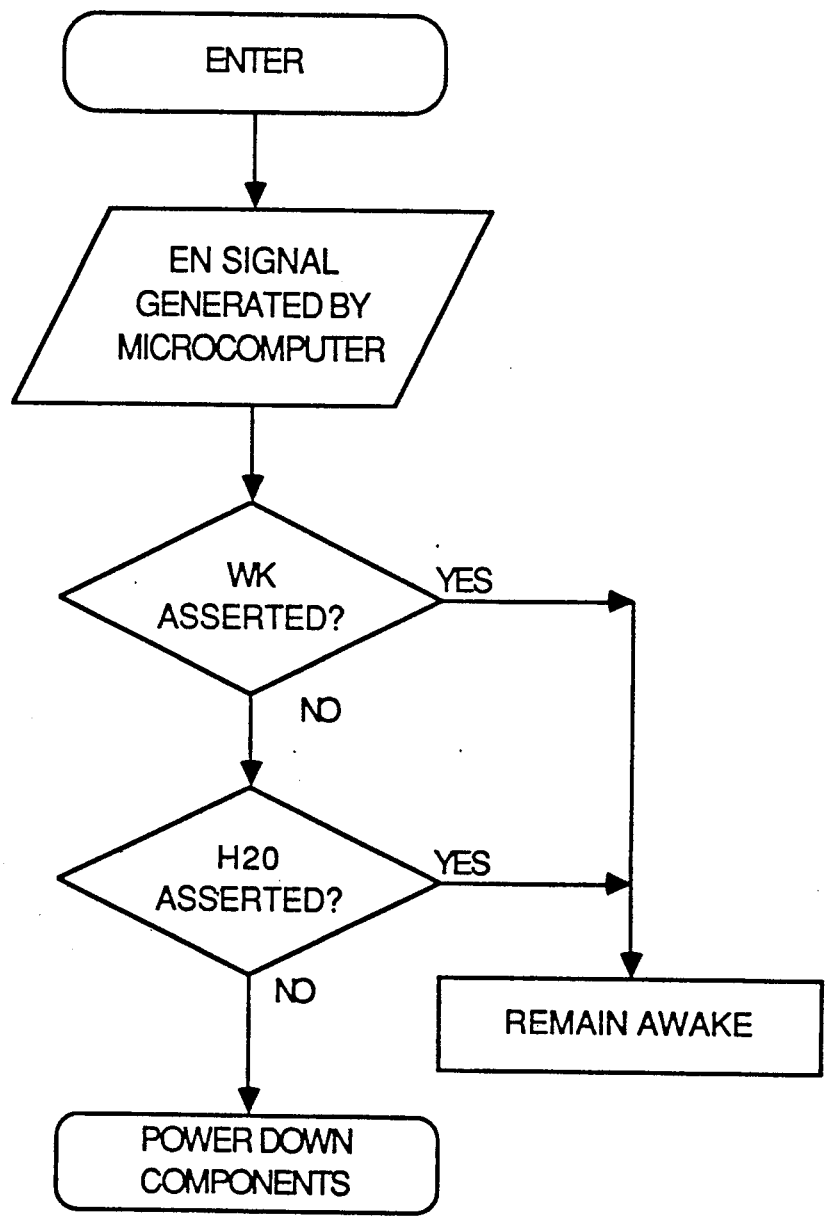
FIG. 8C is a flow diagram of the power down process of the rain sampling device of the present invention.

FIG. 8A comprises a flow diagram further illustrating operation of the rain sampling program in the rain sampling mode. FIGS. 8B and 8C respectively comprise flow diagrams further illustrating the power up and the power down operations of the rain sampling device.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A rain sampling device, comprising:
   (a) a collection chamber for temporarily holding a sample of wet precipitation until said sample is of sufficient size;
   (b) means for diverting wet precipitation into said collection chamber;
   (c) electrical control means for generating control signals for regulating operations of the sampling device;
   (d) valve means including a magnetically actuated plunger for releasing said sample of precipitation from said chamber while blocking further quantities of precipitation from entering said chamber in response to a control signal from said control means;
   (e) a plurality of vessels for permanently retaining samples of wet precipitation; and
   (f) means for distributing various samples of wet precipitation released from said chamber into different ones of said retaining vessels;
   wherein said electrical control means includes a microcomputer means for implementing sampling time schedules for operating said valve means as desired by an operator of the sampling device.

2. The rain sampling device of claim 1, further comprising:
   (g) means for automatically activating and deactivating the rain sampling device by engaging and disengaging electrical power to one or more of the components of said electrical control means so that said device is fully operational only when needed in order to thereby conserve electrical power.

3. The rain sampling device of claim 1, wherein said means for distributing samples includes:
   a rotatable ring gear having a channel for directing liquid sample materials into different passages which are positioned around the periphery of the gear and which lead to different ones of said retaining vessels, said retaining vessels being stationary.

4. A rain sampling system, comprising:
   means for collecting and distributing samples of wet precipitation into vessels for permanently retaining such samples in response to one or more control signals;
   (b) electrical control means for generating control signals for regulating the operation of said means for collecting and distributing samples of wet precipitation, said control means including a microcomputer means which is programmable for implementing different sampling schedules as desired by an operator of the system; and
   (c) means for automatically activating and deactivating the rain sampling system by selectively engaging and disengaging power to various components of said electrical control means in response to signals from a real time clock apparatus, a moisture detection device or said microcomputer means, said automatically activating and deactivating means engaging power to said microcomputer means in response to signals from said real time clock apparatus or said moisture detection device, and disengaging the power to said microcomputer means in response to signals from said microcomputer means.

5. The rain sampling system of claim 4, wherein said means for collecting and distributing samples includes:
   valve means having a magnetically actuated plunger for releasing said samples of wet precipitation from a temporary holding chamber while preventing further samples from entering said chamber in response to a control signal from said electrical control means.

6. The rain sampling system of claim 4, wherein said means for collecting and distributing samples includes:
   a rotatable ring gear having a channel for directing liquid sample materials into different passages which are positioned around the periphery of the gear and which lead to different ones of said retaining vessels.

7. A rain sampling device, comprising:
   (a) a collection chamber having an entrance port and an exit port for temporarily holding wet precipitation while a sufficient quantity is collected to constitute a usable sample of the said precipitation;
   (b) means for diverting said wet precipitation into said collection chamber;
   (c) an elongate plunger having a magnetic core which is vertically disposed within said chamber so as to allow it to be vertically displaced and which includes a pair of conically-shaped ends adapted for engaging and sealing off said entrance and exit ports to said chamber;
   (d) an electrical coil positioned above said chamber for vertically displacing said plunger upwardly by attracting its magnetic core in order to alternatively open and close said exit and entrance ports to said chamber when electrical power is applied to the coil and thereby allow precipitation samples to be controllably collected and released from said chamber;
   (e) a plurality of vessels for permanently retaining samples of wet precipitation; and
   (f) means for distributing various wet precipitation samples from said chamber into different ones of said retaining vessels.

8. The rain sampling device of claim 7, further including:
   (g) electrical control means for controlling electrical power supplied to said coil and thereby controlling the operation of said plunger.

9. The rain sampling device of claim 8 wherein said electrical control means includes timing means for operating said sampling device to take samples on a predetermined time schedule.

10. A rain sampling device, comprising:
    (a) a chamber for temporarily holding a sample of wet precipitation until said sample is of sufficient size;
    (b) means for diverting wet precipitation into said collection chamber;
    (c) electrical control means for generating control signals for regulating operations of the sampling device;
    (d) valve means including a magnetically actuated plunger for releasing said sample of precipitation from said chamber while blocking further quantities of precipitation from entering said chamber in response to a control signal from said control means;
    (e) a plurality of stationary vessels for permanently retaining samples of wet precipitation; and
    (f) means for distributing various samples of wet precipitation released from said chamber into different ones of said retaining vessels, said means for distributing samples including a rotatable ring gear having a channel for directing liquid sample materials into different passages which are positioned around the periphery of the gear and which lead to different ones of said retaining vessels.

* * * * *